United States Patent [19]

Chen

[11] 4,418,699
[45] Dec. 6, 1983

[54] TWIN GAUGE AND TWIN NEEDLE SPHYGMOMANOMETERS

[76] Inventor: Hsu C. Chen, 4th Fl., 11, Lane 132, Sung-Chiang Rd., Taipei, Taiwan

[21] Appl. No.: 352,099

[22] Filed: Feb. 25, 1982

Related U.S. Application Data

[63] Continuation of Ser. No. 64,529, Aug. 7, 1979, abandoned.

[51] Int. Cl.³ .............................................. A61B 5/02
[52] U.S. Cl. ..................................... 28/685; 128/677
[58] Field of Search ........................ 128/672, 677–685

[56] References Cited

U.S. PATENT DOCUMENTS

| | | | |
|---|---|---|---|
| 3,056,401 | 10/1962 | Greenspan et al. | 128/681 |
| 3,542,011 | 11/1970 | Langenbeck | 128/677 |
| 3,823,707 | 7/1974 | Hayes | 128/685 |
| 3,901,217 | 8/1975 | Clark | 128/677 |
| 3,918,436 | 11/1975 | Peart et al. | 128/677 |
| 4,010,739 | 3/1977 | Leach | 128/677 |
| 4,013,265 | 3/1977 | Speidel | 128/685 X |
| 4,090,503 | 5/1978 | Speidel | 128/684 |
| 4,098,291 | 7/1978 | Clark et al. | 128/685 |
| 4,111,057 | 9/1978 | Affeldt et al. | 128/680 X |
| 4,116,217 | 9/1978 | Speidel | 128/685 X |
| 4,222,390 | 9/1980 | Berliner et al. | 128/677 |

FOREIGN PATENT DOCUMENTS 135581 5/1961 U.S.S.R. .

*Primary Examiner*—Lee S. Cohen
*Assistant Examiner*—Angela D. Sykes
*Attorney, Agent, or Firm*—Cushman, Darby & Cushman

[57] ABSTRACT

A twin gauge and a twin needle sphygmomanometer. In the twin gauge embodiment separate systolic and diastolic gauges are provided. Both gauges are synchronized during initial pressurization of a pressure cuff and during the first portion of cuff depressurization. Upon detection of the first Korotkov sounds, the closing of a tangent valve "freezes" the systolic gauge for later reading. Upon detecting the last Korotkov sounds, a cotter valve coupling an air pump to the pressure cuff is closed, freezing the diastolic pressure on the diastolic gauge. In the twin needle embodiment, systolic and diastolic needles are synchronized during initial pressurization of the pressure cuff. As pressure in the cuff is bled both needles remain synchronized until the first Korotkov sounds are heard. Then, actuation of a clutch mechanism freezes the systolic needle. Upon detecting the last Korotkov sounds, the main cotter valve is closed to freeze the diastolic needle.

4 Claims, 22 Drawing Figures

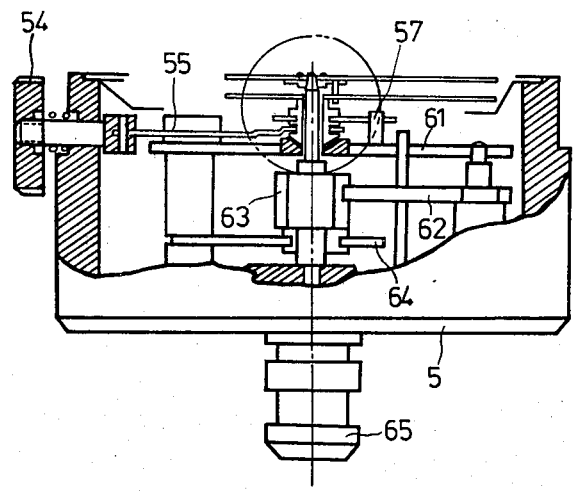
Fig. 5
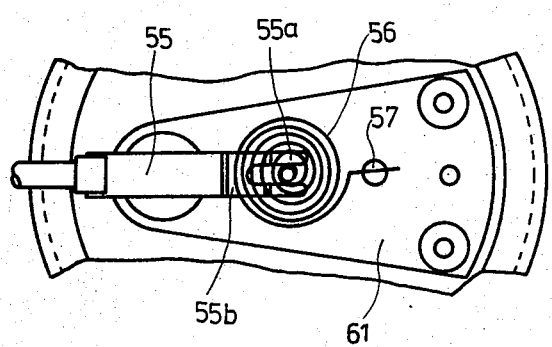
Fig. 5-A
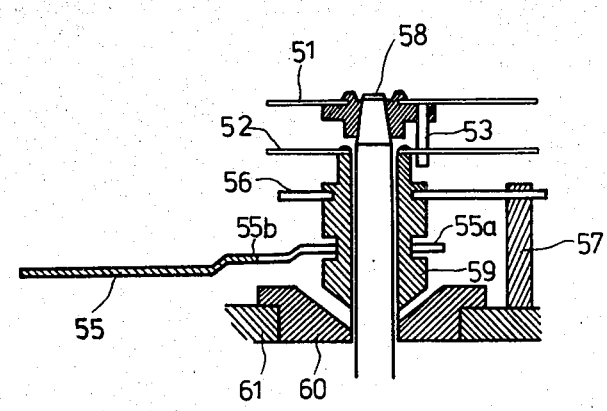
Fig. 5-B

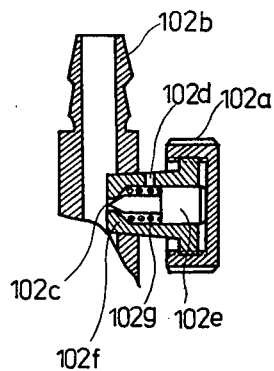
Fig. 6
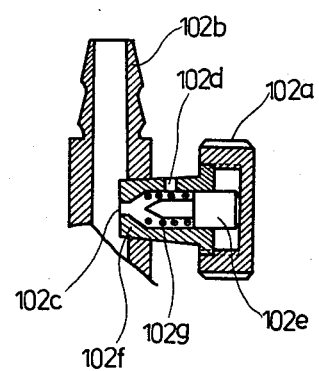
Fig. 6-A
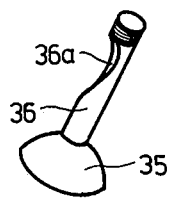
Fig. 7-B
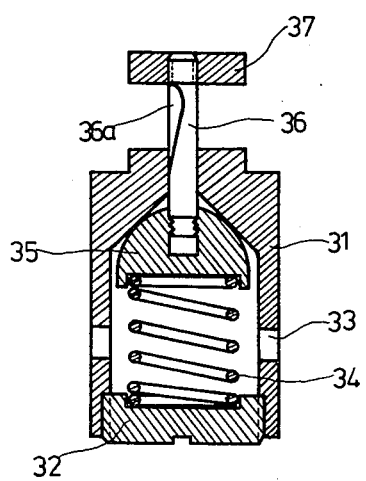
Fig. 7
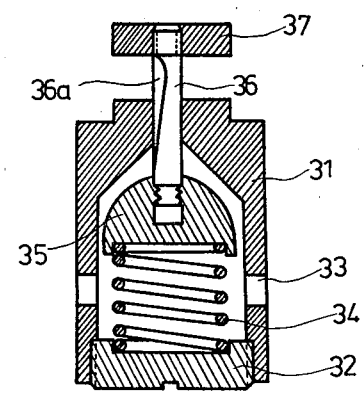
Fig. 7-A

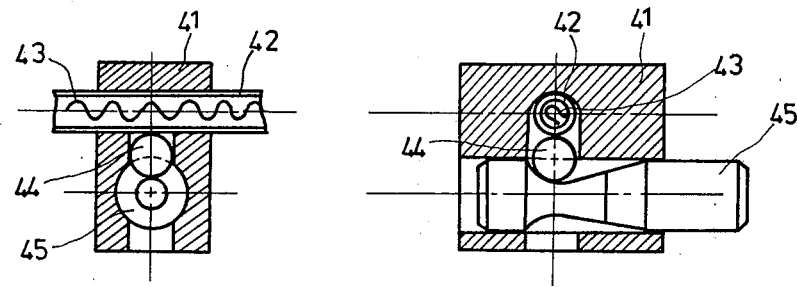
Fig. 8-A
Fig. 8
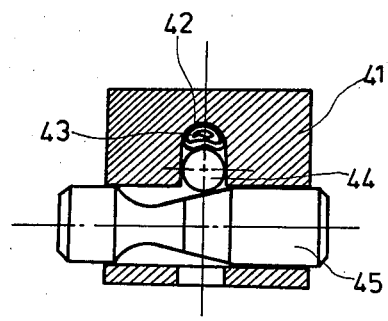
Fig. 8-B
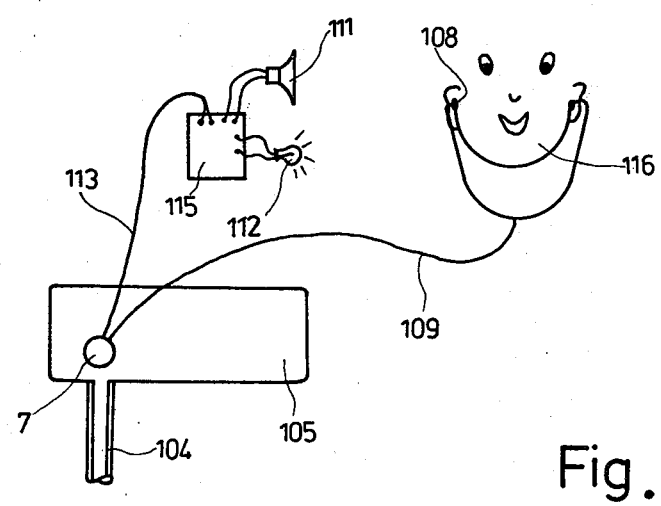
Fig. 9-C

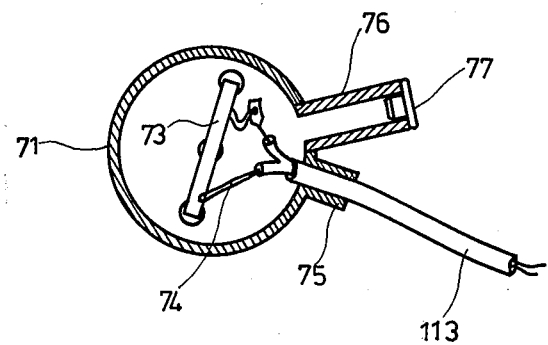
Fig. 9
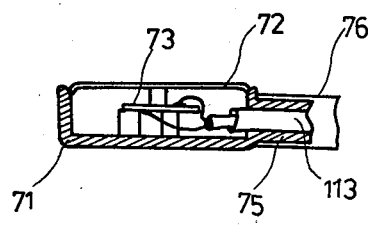
Fig. 9-A
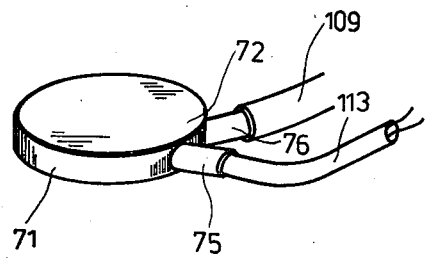
Fig 9-B

TWIN GAUGE AND TWIN NEEDLE SPHYGMOMANOMETERS This is a continuation, of application Ser. No. 64,529 filed Aug. 7, 1979, now abandoned.

BACKGROUND OF THE INVENTION

As shown in FIGS. 1 and 2 conventional aneroid sphygmomanometers comprise a single gauge having a single needle. Therefore, when a patient must measure his own blood pressure, he must carefully watch the needle movement and memorize the systolic and diastolic pressures as the needle drops.

A patient unskilled in measuring blood pressure is apt to make mistakes in memorizing the blood pressure values. Especially in the case of an older patient, or those who cannot see well, a faulty measurement is likely to occur.

SUMMARY OF THE INVENTION

Therefore, the present invention provides a twin gauge sphygmomanometer and a twin needle sphygmomanometer. Each of these two embodiments maintains systolic and diastolic measurements separately and "freezes" them so that there is no need for a patient to memorize gauge pressure values as a needle drops during de-pressurization of his cuff.

The primary object of this invention is to provide two separate synchronized gauges or two separate synchronized needles to mechanically memorize both the systolic and diastolic blood pressure readings.

In the two gauge embodiment, providing two gauges it is possible, to check and to compare the readings of both gauges as an indication of gauge accuracy. If the gauges do not synchronize and their differences exceed predetermined allowable tolerances, the unit can be returned to repair.

Both embodiments of this invention utilize a novel cotter valve, in place of a conventional screw valve for controlling the pressurization and bleeding of the pressure cuff in the sphygmomanometer. This cotter valve can be operated by one touch pushing, to achieve the rapid closing and opening of the valve. In addition, its unique cotter opening can assure either uniform slow flow or rush-flow of releasing air.

The tangent valve used in the two gauge embodiment has a very simple mechanism including a tangent ball to contact a unique air tube tangentially. It can effectively perform quick shut-off and re-opening of the air passage, between two gauges, so as to rapidly achieve separation or synchronization.

An auscultatory device is added to the microphone of a conventional electronic sphygmomanometer, to enable either the checking of its accuracy or to re-adjust the sensitivity of the electronic circuit to obtain correct measurement of blood pressure.

BRIEF DESCRIPTION OF THE DRAWINGS

These and other objects of the present invention will become more apparent, from the following description of the preferred embodiments taken in conjunction with the accompanying drawings in which:

FIG. 3A depicts a schematic view of stethoscope to be inserted, at the position of the microphone, in case of measuring with twin-gauge synchronized aneroid sphygmomanometer, according to the present invention.

FIG. 3B depicts a cross-sectional view of the tangent valve switched to the closed position, according to the present invention.

FIG. 4A depicts a schematic view of stethoscope to be inserted, at the position of the microphone, in case of measuring with twin-needle synchronized aneroid sphygmomanometer, according to the present invention.

FIG. 5 depicts a partial cross-sectional view of twin-needle gauge, to show the mechanism of two needles, at its synchronized position, according to the present invention.

FIG. 5A depicts a partial top view without needles, to show the fork clutch mechanism of the twin-needle gauge, according to the present invention.

FIG. 5B depicts a close-up view of the lower needle spindle, to show the synchronization of two needles, according to the present invention.

FIG. 6 depicts a cross-sectional view of the conventional screw type needle valve, in the status of closing position.

FIG. 6A depicts a cross-sectional view of the conventional screw type needle valve, in the status of releasing position.

FIG. 7 depicts a cross-sectional view of the cotter valve, in the status of the normal-close position, according to the present invention.

FIG. 7A depicts a cross-sectional view of cotter valve, in the status of releasing position, according to the present invention.

FIG. 7B depicts a perspective view of the tail-enlarged cotter shape opening, at the valve stem of the cotter valve, according to the present invention.

FIG. 8 depicts a cross-sectional front view of the tangent valve, in the status of the normal-open position, according to the present invention.

FIG. 8A depicts a cross-sectional side view of the tangent valve, in the status of the normal-open position, according to the present invention.

FIG. 8B depicts a cross-sectional front view of the tangent valve, in the status of the close position, according to the present invention.

FIG. 9 depicts a cross-sectional front view of the auscultatory device, according to the present invention.

FIG. 9A depicts a cross-sectional side view of the auscultatory device, according to the present invention.

FIG. 9B depicts a perspective view of the auscultatory device, with connecting a part of Y tube of the stethoscope.

FIG. 9C depicts a schematic view of checking the accuracy of the electronic sphygmomanometer, with the auscultatory device, according to the present invention.

DETAILED DESCRIPTION OF THE INVENTION

Twin-gauge Embodiment

Figure 1:
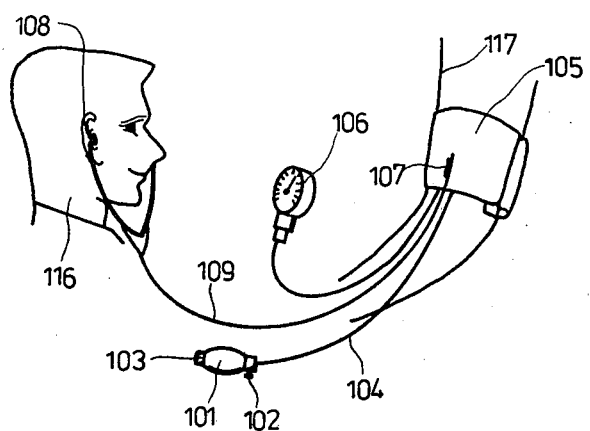
FIG. 1 depicts a schematic view of measuring arterial blood pressure, with the conventional stethoscopic single aneroid sphygmomanometer.
Figure 2:
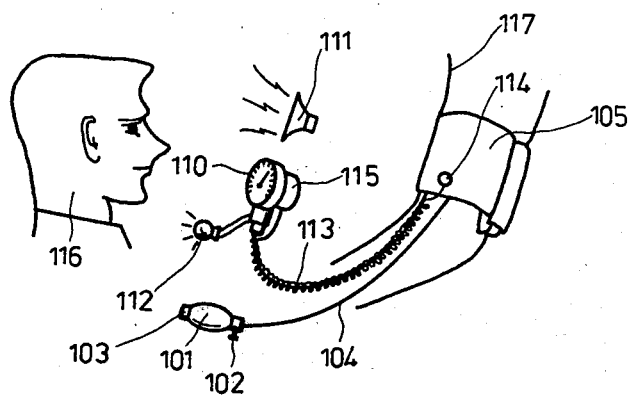
FIG. 2 depicts a schematic view of measuring arterial blood pressure, with the conventional electronic single aneroid sphygmomanometer.
Figure 3:
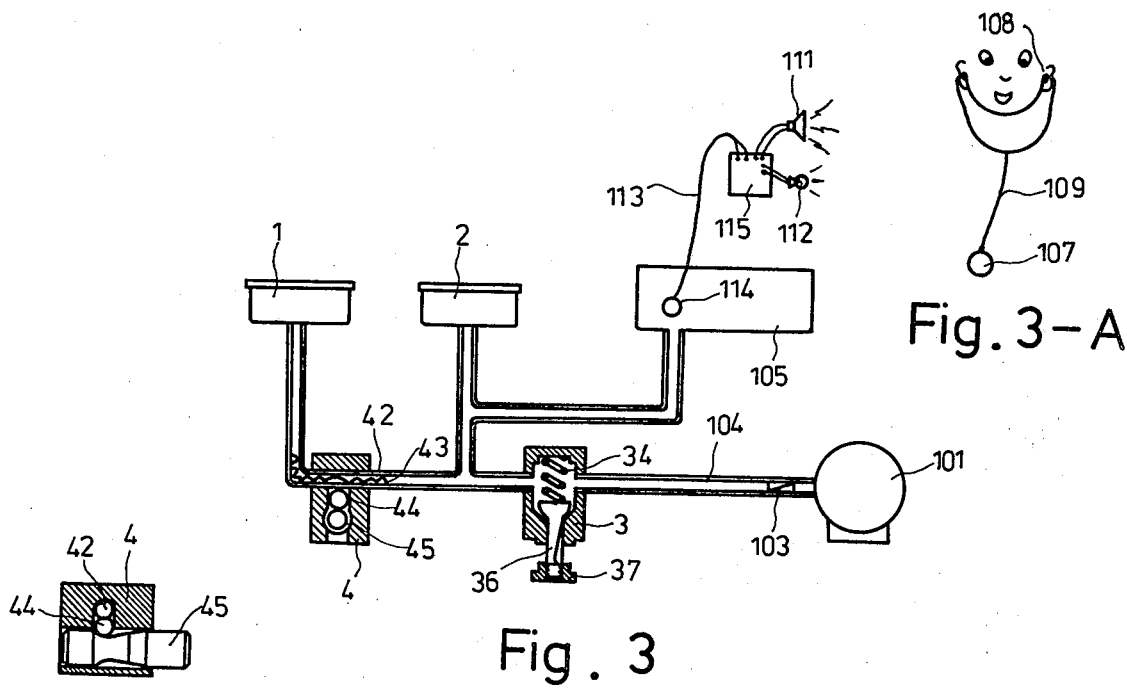
FIG. 3 depicts a flow diagram of measuring arterial blood pressure, with the electronic twin-gauge synchronized aneroid sphygmomanometer, according to the present invention.

Referring now to FIG. 3, there is show a twin-gauge synchronized aneroid sphygmomanometer according to the present invention.

The pneumatic parts include a systolic gauge 1, diastolic gauge 2, cotter valve 3, tangent valve 4, air pump 101, check valve 103, rubber tube 104 and cuff 105.

The sensory parts include a microphone 114, electronic circuit 115, speaker 111, lamp 112 and main lead 113, for electronic sphygmomanometer, however a stethoscopic sphygmomanometer includes a stethoscope head 107, Y tube 109 and stethoscope eartips 108 as shown in FIG. 3A.

Air pump 101 pumps pressurized air out through check valve 103 and cotter valve 3. The pressurized air flows into the systolic gauge 1, the diastolic gauge 2 and the cuff 105, which contains a rubber bladder inside, and is wrapped around the arm of the patient.

As the cuff is inflated, both the needle of gauge 1 and gauge 2, go up in synchronism, to indicate the same value of increased blood pressure reading in mm Hg. When the pressure reading reaches to approximately 20 to 30 mm Hg higher than the patient's usual diastolic value, which pressure is enough to prevent the blood to flow toward the unwrapped forearm of the patient, then pumping is stopped. Therefore both gauges also stop moving and indicate the same reading blood pressure value (e.g. 170 mm Hg.).

After cuff 105 is pressurized, valve pusher 37 is pushed to open the cotter valve 3 slightly, letting the air release from the cotter valve 3, to start deflating the cuff, at a rate of 2 to 3 mm Hg per heart-beat. Meanwhile the needles of both gauges are going down synchronously.

As soon as the deflated cuff pressure sufficiently reduces, the blood flows through again. At the same time the first Korotkov sounds are heard from the speaker 111, for indicating the systolic blood pressure of the patient. Immediately the valve stem 45 is pushed to close the tangent valve causing the needle of the gauge 1 to stop at the position of the systolic blood pressure value. Meanwhile the compression cuff still continues to deflate with Korotkov sounding and the gauge 2 continues to go down.

As soon as the Korotkov sounds disappear to indicate the diastolic blood pressure of the patient, the stem button 37 is released, to close the cotter valve 3, causing the needle of the gauge 2 stop at the position, to point the diastolic value.

After carefully recording the measured systolic and diastolic blood pressure values separately, from gauge 1 and 2, the stem button of the cotter valve 3 is pushed with a deep stroke to full open the tail-enlarged cotter shape opening of cotter valve 3, to release the rest of pressurized air in the cuff 105. Then, the wrapped cuff is removed to finish the measurement of blood pressure. The cotter valve construction detail is explained with reference to FIGS. 6–7B and the tangent valve construction detail is explained with reference to FIGS. 8–8B.

The present invention has two major merits.

The one is to be able to keep the systolic and diastolic values of measured blood pressure, separately at each gauge, even after measurement and to eliminate the mis-reading and mis-memory by a patient especially, who has vision or hearing defect.

The other is to be able to check and compare the each gauge's indication accuracy, during or before measurement. If the gauges do not synchronize and their differences exceed the allowable tolerances, the unit can be returned to the factory for repair. Indeed the synchronization of two gauges can also avoid the inaccuracies in measuring the blood pressure.

Operation of the twin-gauge system is simpler than that of the conventional single-gauge sphygmomanometer, in part because of the new designed cotter valve and tangent valve in the pneumatic control system.

It is important that the accuracy of individual gauge be within ±1 mm Hg, otherwise the two gauges cannot by synchronized. For this reason the twin-gauge system is superior in accuracy than the conventional single sphygmomanometer system.

The present invention of the said twin-gauge system can be used in both the electronic sphygmomanometer and the stethoscope sphygmomanometer to assure more convenient service.

Figure 4:
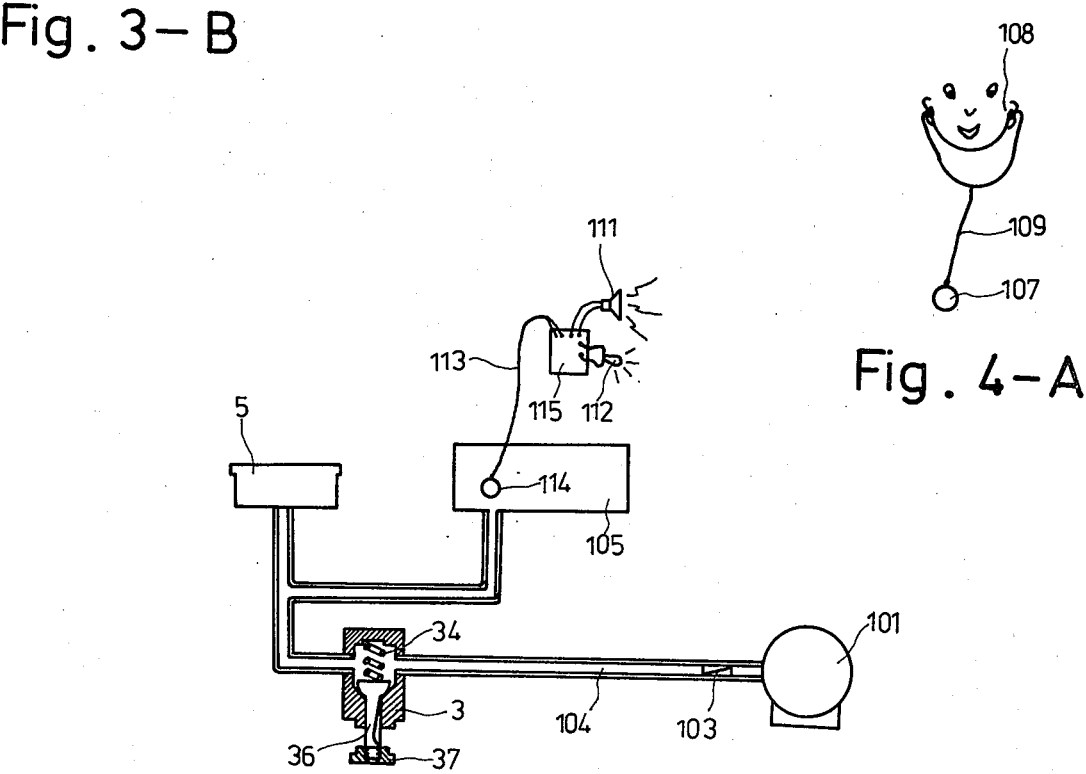
FIG. 4 depicts a flow diagram of measuring arterial blood pressure with the electronic twin-needle synchronized aneroid sphygmomanometer, according to the present invention.

Referring now to FIG. 4, there is shown a twin-needle synchronized aneroid sphygmomanometer according to the present invention.

The components of the twin-needle synchronized aneroid sphygmomanometer are almost as same as the above mentioned twin-gauge synchronized aneroid sphygmomanometer, except for the gauge 5 which has different mechanism, to actuate the synchronization and separation of its two needles.

Referring now to FIG. 5, there is shown the driving mechanism of the twin-needle gauge. The driving mechanism includes the following major parts: diastolic needle (or upper needle) 51, systolic needle (or lower needle) 52, drive pin 53, clutch button 54, fork clutch 55, lower needle spring 56, spring lock pin 57, upper needle spindle 58, lower needle spindle 59, lower needle bearing 60, upper bearing plate 61, sector gear 62, pinion gear 63, pinion gear spring 64 and gauge connecter 65.

Referring again to FIG. 4, from air pump 101, the pressurized air is sent out through check valve 103, air tube 104, cotter valve 3 and then flows into twin-needle gauge 5 and cuff 105.

Whereas as shown in FIG. 5 & FIG. 5B the upper needle 51, is fixed to the upper needle spindle 58, which is integral with pinion gear 63. A drive pin 53 is fixed eccentrically under the boss of the upper needle 51 and has a length long enough to be tangent at the right side of the lower needle 52. The lower needle 52 is fixed at the top of the hollow lower needle spindle 59, in which the upper needle spindle is inserted to rotate freely.

As pumping to inflate the cuff and the gauge proceeds, the built-up pressure causes the bellow of gauge 5, to actuate the pinion shaft to rotate clockwise. Therefore this rotation of pinion shaft causes the upper needle 51 to rotate integrally with the drive pin 53, which drives the lower needle to rotate clockwise. Thus the two needles rotate clockwise with one above another in synchronism to indicate the same value of increased cuff pressure reading in mm Hg. When the pressure reading reaches to approximately 20 to 30 mm Hg higher than the patient's usual diastolic value, pumping is stopped. At this moment the upper needle laps over the lower needle and both stop moving.

Then the stem button 37 is pushed to open the cotter valve 3 and let the pressurized air release. As cuff deflates, the upper needle 51, which is fixed at the top of pinion gear shaft 58, is driven by the spring back force of the pinion gear spring 64 as shown in FIG. 5A, and therefore is forced to rotate counter-clockwise, to indicate the decreasing cuff pressure.

Meanwhile the lower needle is free from the restraint of drive pin 53 for clockwise rotation, because the upper needle has already changed to rotate counter-clockwise.

A counter-clockwise spring 56 is set between the lower needle spindle 59 and spring lock pin 57, which is locked on the upper bearing plate 61, as shown in FIG. 5B.

So the freed lower needle 52 is now driven by the spring-back force of the spring 56 and is forced to rotate counter-clockwise.

However the rotating speed of the lower needle is always restrained from the drive pin 53 of the upper needle, therefore the lower needle can never run over the upper needle and always follows to drive pin 53 closely, and rotates counter-clockwise, with one above another, in synchronism to indicate the same blood pressure value during the deflation.

Of course the twisting torque of spring 56 should be designed just enough to force the lower needle to rotate counter-clockwise and should not be over-strong than the twisting torque of the pinion gear spring 64 which drives the upper needle.

During the deflation, the two needles go down synchronously with lapping one above another, until the first Korotkov sounds are heard and the clutch button 54 is pushed to stop the movement of the lower needle, therefore the lower needle stays at the position of the systolic blood pressure reading.

The mechanism of stopping the lower needle alone, while the upper needle keeps go on, is actuated by the following steps.

Push the clutch button 54, and let the fork clutch 55, move forward. The upper part 55a of the fork clutch slips off the slot of the lower needle spindle 59, in order to bring the lower part 55b of the fork clutch to engage in the slot of the lower needle spindle and let the spindle 59 come down and fit into the conical bearing 60. Therefore the friction force between the end conical spindle of the lower needle and the sunken conical bearing surface can effectively prevent the spindle to move any more and let the lower needle stop immediately.

Meanwhile the compression cuff still continues to deflate with the Korotkov sounds sounding and the upper needle 51 going down. As soon as the Korotkov sounds disappear to indicate the diastolic blood pressure, close immediately the cotter valve 3, by releasing the valve stem 37, and let the upper needle 51 stop at the position to indicate the diastolic value of blood pressure.

After carefully recording the measured systolic and diastolic blood pressure values separately from the positions of the lower and upper needle, push the stem button of the cotter valve 3 to release the rest of pressurized air in the cuff 105, at a breath, and then take off the wrapped cuff to finish the measurement of blood pressure.

The merit of this twin needle embodiment present invention is to be able to keep the systolic and diastolic blood pressure value separately at each needle, even after measurement and to eliminate the mis-reading and mis-memory by a patient especially who has vision or hearing defect.

The twin-needle embodiment can be used in both the electronic sphygmomanometer and the stethoscopic sphygmomanometer, to actuate the effectiveness of the delicate two-gauges operation.

In addition, the present invention can be manufactured to a very compact size, for travelling usage, owing to the combination of one touch operation clutch mechanism with an unique cotter valve.

Referring now to FIG. 7, there is shown construction detail of the cotter valve.

As shown in FIG. 7, the said cotter valve consists of valve body 31, valve cap 32, valve port 33, valve spring 34, rubber plug 35, cotter stem 36 and stem button 37.

The cotter valve is normally closed and actuated by the spring force of valve spring 34 to keep the semi-sphere rubber plug 35 contacting tightly with the conical surface of the metallic valve body 31.

Rubber plug 35 is integral with the cotter stem 36 which has a short cylindrical portion at the bottom and a long tail-enlarged cotter shape opening 36a at the top portion, as shown in FIG. 7B.

During the deflating cycle of blood pressure measuring, whenever the releasing of pressurized air is required, one can push the stem button 37 to compress the valve spring 34 and let the integrity of rubber plug 35 and valve stem 36, drop to open a passage between the valve body 31 and the integrity, for releasing air as shown in FIG. 7A.

The unique design of cotter-shaped opening 36a, is shown in FIG. 7B. Cotter-shaped opening 36a is cut valve stem 36, in order to effectively adjust the rate of deflating air, depending on the pressure of air and the depth of pushing stroke of valve stem 36.

Whenever it is necessary to close the cotter valve, one can release his finger from stem button 37 and let the valve spring 34 restore the integrity of the rubber plug 35 and the valve stem 36 to the normal-close position.

The cotter valve contributes substantially to the effectiveness of the present invention.

The unique tail-enlarged cotter shape opening combined with the pushing stroke of cotter stem can effectively adjust the deflating quantity from constant to any variation as quickly as accurately.

The operation of opening and closing of valve can be done very quickly and simply, by one touch-on or touch-off operation of a finger tip.

Even though the cotter valve was originally invented for use in the twin-gauge and twin-needle systems, because of its excellent effectiveness as described above, it can improve the practical operating efficiency for any type of sphygmomanometer of both stethoscopic and electronic as well as mercury-gravity type.

Referring now to FIG. 8 there is shown the detailed construction of the tangent valve. The tangent valve includes a valve body 41, rubber tube 42, S-shape spring 43, ball 44 and valve stem 45.

One piece of S'-shape spring 43 is inserted into the rubber tube 42. A ball 44 is held by the stream lined part of the valve stem 45 and contacts tangently to the rubber tube 42 to constitute the normal-open status of the tangent valve.

When the valve stem 45 is pushed to the left, as shown in FIG. 8B, the ball 44 is forced to slide up along the stream lined part of valve stem 45, and forced to move ahead to press rubber tube 42, which becomes flat enough to close the passage of the rubber tube, in order to bring the tangent valve to closed position.

When the other end of the valve stem 45 is pushed back as shown in FIG. 8, the ball 44 is restored to the original position. meanwhile the S-shape spring in the rubber tube is freed and immediately spring back to restore the passage of the rubber tube 42 in full open.

The excellent effectiveness of the tangent valve is the unique high efficiency of quick shut-off and quick re-open function. Because the tangent valve has very simple mechanism, it can close very rapidly by one touch pushing-operation and re-open immediately, by the restoration of S-shape spring inside the rubber tube.

The tangent valve is an essential element which renders the two-gauge synchronized aneroid sphygmomanometer embodiment practical use. Because only such a tangent valve with quick shut-off and quick re-open mechanism can meet the qualification of immediately synchronization as well as separation for the said twin-gauge system.

In addition to its use in the two sphygmomanometers, the tangent valve can be applied to valuable use in other air systems, which requires high frequency of the quick opening and closing cycles, owing to its outstanding merits of simple construction, accurate function, less-maintenance and lower cost.

Referring now to FIG. 9 there is shown the auscultatory device used in the sphygmomanometer according to the present invention. The auscultatory device includes a microphone case 71, diaphram 72, ceramic piece 73, lead line 74, outlet for electronic main lead 75, auscultatory connecter 76 and connecter plug 77.

Practically the auscultatory device 7 has almost same components as a conventional microphone used in an electronic sphygmomanometer, except for the addition of an auscultatory connecter as shown in FIG. 9B.

Before checking with the auscultatory device one should confirm the performance of the speaker 111 is synchronized with the lamp 112, that is the speaker 11 always sounds simultaneously with the lighting of the lamp 112, of the electronic sphygmomanometer itself, which is to be checked.

Then, one can take off the connector plug 77 from auscultatory connecter 76 and connect to the Y-tube 109 of stethoscope as shown in FIG. 9B.

Then one can insert the microphone 7 into the cuff 105 with diaphram 72 faced to the artery of the patient's arm. Then air is pumped to inflate air into the cuff. Then the circuit of the speaker 111 is switched off, in order to prevent the sounding of Korotkov sounds from the speaker. However the switch on the circuit of the lamp 112 should be kept on, as shown in FIG. 9C.

During deflating cycle of blood pressure measurement, it should be noted whether the Korotkov sounds heard from the stethoscope 108 synchronize with the lighting of lamp 112 or not. If Korotkov sounds synchronize with the lighting of lamp all the way, the sensitivity and accuracy of the electronic circuit of the sphygmomanometer is perfectly O.K. In this case the correct measuring of blood pressure can be assured. Otherewise, the electronic sphygmomanometer should be re-conditioned or the sensitivity of speaker should be readjusted.

In order to determine the efficiency of the auscultatory device, some samples were manufactured, and put into test with various electronic sphygmomanometer. The result is successful as follows:

If the circuit of the electronic system is correct, the Korotkov sounds can be heard by anyone who puts the stethoscope tips in this ears, and it can be easily recognized that the lighting of the lamp synchronizes perfectly with the Korotkov sounds. Thus the auscultatory device can be easily used by anybody for checking the accuracy of the electronic circuit of the sphygmomanometer as well as for adjustment of the sensitivity of the speaker.

During usage or preservation, the electronic sphygmomanometer may deviate from accuracy, influenced by the temperature, humility or interferency from other electricity etc. If such a deviation occurs, the blood pressure reading indicated by the gauge will not be correct. The false measurement in checking patient's blood pressure may result in serious mistreatment etc.

Therefore it is very practical as well as very important that the electronic sphygmomanometer should be always checked by the said auscultatory device in order to assure the measurement of accurate blood pressure.

While the invention has been described in connection with what is presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

I claim:

1. A sphygmomanometer, comprising:
    a pressure cuff adapted to be worn by a patient;
    an air pump for pressurizing said cuff;
    a valve means and tube means coupling said air pump to said cuff for controlling the flow of air to and from said cuff; and
    a guage means coupled via tube means to said cuff for indicating the pressure in said cuff, said gauge means comprising:
    a diaphragm responsive to cuff pressure,
    an upper diastolic needle means with a shaft and a pinion gear for indicating diastolic blood pressure, the shaft being driven by the motion of said diaphragm,
    a lower systolic needle means rotatable independently of said upper needle means for indicating systolic blood pressure;
    drive means, coupled to said upper needle means, for engaging and driving said lower needle means when said upper needle means moves only in a first direction indicative of increasing pressure and not in a second direction opposite to said first direction;
    lower needle spring return means for biasing said lower needle means in said second direction indicative of decreasing pressure; and
    an actuatable clutch assembly means for stopping the motion of only said lower needle means moving in said second direction upon the detection by the user of Korotkov sounds, said lower needle means then indicating a systolic blood pressure, while said upper needle means continues to measure the pressure in said cuff, the motion of said upper needle means in said second direction stopping only when the pressure in said cuff ceases to change such as by the closing of said valve means, said valve means typically being closed upon the occurrence of the last Korotkov sound, thereby causing said upper needle means to indicate diastolic blood pressure, said clutch assembly means comprising a lower needle body element having a bore therethrough, said shaft integral with said upper needle means passing through said bore, said body element having a lower needle spindle at a bottom portion thereof; a lower needle bearing receiving said spindle such that when said spindle and bearing are engaged with one another there is sufficient friction therebetween to stop any relative rotation between said body element and lower needle means even if said shaft and upper needle means are moving; and an actuatable fork clutch means for pressing said spindle into contact with said bearing, whereby when said fork clutch means is actuated, said lower needle means stops any motion thereof.

2. A sphygmomanometer according to claim 1 wherein said clutch assembly means further includes a clutch button means for actuating said fork cluch means.

3. A sphygmomanometer according to claim 1 wherein said drive means comprises a drive pin coupled to said upper needle means, the drive pin being sufficiently long to engage said lower needle means and push it in said first direction.

4. A sphygmomanometer according to claim 1 wherein said valve means comprises:
- a hollow valve body having an upper portion and a lower portion, said valve body having a valve port therein;
- a valve cap means for closing the lower portion of said valve body;
- a semi-spherical rubber plug movable within said valve body;
- a valve spring means for biasing said rubber plug toward the upper portion of said valve body, thereby normally biasing said valve means closed.
- a cotter stem having a tail-enlarged cotter-shaped cutaway region therein, said stem being integral with said rubber plug and having a tail extending through the upper portion of said valve body, the amount of extension of said stem through the upper portion of said valve body determining the amount of cutaway region of said stem exposed to the outside of said valve body; and
- a stem button means coupled to the tail of said stem for adjusting the extension of said stem into and out of said valve body by pressing said stem and rubber plug against the bias of said spring means, the pressing of said stem button means causing the stem and rubber plug to be displaced against the bias of said spring means causing an increasing portion of said cutaway region to be exposed within the valve body.

* * * * *